United States Patent [19]

Cobia

[11] Plant 4,602

[45] Oct. 21, 1980

[54] PLANT VARIETY OF THE ACANTHUS FAMILY

[76] Inventor: Barnell L. Cobia, P.O. Box 1307, Winter Garden, Fla. 32707

[21] Appl. No.: 36,541

[22] Filed: May 7, 1979

[51] Int. Cl.[3] ..... A01H 5/12

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new plant variety of the Acanthus family has plant parts that in size and shape are generally comparable to those of the "Nerve plant" and a leaf blade with the mosaic leaf venation pattern that is characteristic of the "Nerve plant" but which is nevertheless variegated and provided with chlorophyllous areas that are lighter than the chlorophyllous areas of the "Nerve plant", the achlorophyllous areas appearing as blotches or specks that are generally marginally located in the leaf blade.

3 Drawing Figures

This invention relates to a new and distinct plant variety of the Acanthus family and which has been developed from a vegetative mutation that appeared on a plant specimen of the *Fittonia verschafeltii argyroneura* variety that is commonly called the "Nerve plant". The "Nerve plant" specimen was under cultivation in a nursery at Winter Garden, Fla. at the time of the discovery and since then, the new variety has been asexually reproduced at the same nursery and by the propagation of stem cuttings taken from the specimen.

Plant specimens of the "Nerve plant" are related to the *Fittonia verschafeltii* variety that is commonly called the "Mosaic plant" and also the *Fittonia verschafeltii pearcei* variety that is commonly referred to as the "Snake Skin plant". All of these varieties are characterized by a mosaic venation pattern in a leaf blade that has a basic chlorophyllous field which is solid except for the discontinuities along the veins of the blade. The "Nerve plant" differs from the "Mosaic plant" and "Snake Skin plant" by veins that are generally considered to be white whereas the veins of the last two mentioned varieties are generally reddish or pinkish in coloration.

Yet other related varieties are the *Fittonia verschafeltii argyroneura* 'Minima' variety and the recently introduced *Fittonia verschafeltii argyroneura* 'Angel Snow' variety. Both of these varieties are distinguishable from the "Nerve plant" by their substantially smaller comparative sizes and the 'Angel Snow' variety is mainly distinguishable from the 'Minima' variety by a variegated leaf blade with a mosaic leaf venation pattern that is characteristic of the "Nerve plant" and the 'Minima' variety but which has a basic chlorophyllous field that in color is visibly lighter than that of the "Nerve plant" and 'Minima' variety, the variegated leaf blade being in particular distinguished by marginally located achlorophyllous blotches or specks.

One object of the invention has been to develop a new variety of the Acanthus family for the foliage plant market and which is distinguishable from the known varieties of this family. This object has been fully realized by the invention as will be apparent from the following plant description contained herein and where it will be seen that the new plant variety is distinguishable from its antecedents and known related varieties by a growth habit that provides specimens which have plant parts that, in size, are comparable to those of the "Nerve plant", which have a variegated leaf blade with the mosaic leaf venation pattern that is characteristic of the "Nerve plant" but a basic chlorophyllous field that in color is visibly lighter than the basic field of the "Nerve plant" and 'Minima' variety, the variegated leaf blades of the new variety being particularly distinguishable by marginally located achlorophyllous blotches or specks which are characteristic of the 'Angel Snow' variety.

The accompanying drawings serve by color photographic means to illustrate the new variety, one sheet showing a plant specimen of the new variety, another showing another view of the leaf blades of the variety, and yet another sheet illustrating the inflorescence.

The following is a detailed description of the new variety and is based on observations of well fertilized specimens which were grown in the central Florida area under approximately 85 percent shaded nursery conditions and where temperatures are generally maintained in the range of from about 15° C. to 30° C. during the winter months and from about 24° C. to 36° C. during the summer months. The description is further based on the observations of specimens that were generally from 3–6 months in age as determined from initial propagation.

Except where general terms of ordinary dictionary significance are obviously used, color terminology and color designations reported herein are in accord with the ISCC-NBS Method of Designating Colors as described in the U.S. Dept. of Commerce, National Bureau of Standards, Circular 553, entitled ISCC-NBS "Method of Designating Colors and Dictionary of Colored Terms" with the color designations having been derived from interpretation of Munsell Color Notations obtained by comparing plant specimens with the color specimens in the current "Neighboring Hues Edition" of the Munsell Book of Color, published by Munsell Color Company, Inc. of Baltimore, Md., and to which the reported notations (Munsell Hue, Munsell Value/-Munsell Chroma) are referenced.

Plant Description

Name: *Fittonia verschaffeltii argyroneura* 'Variegata'.

Origin: A vegetative mutation that appeared on a plant of the *Fittonia verschaffeltii argyroneura* variety.

Classification:

A. *Botanic.*—*Fittonia verschaffeltii* var. *argyroneura* E. Coem. Acanthus family (Acanthaceae).

B. *Commercial.*—Foliage plant.

Form: Herbaceous, tropical perennial evergreen with adventitious root system.

Stem:

A. *General.*—Caulescent and herbaceous.

B. *Texture.*—Pubescent with 4 longitudinally oriented rows of wooly hairs that are circumferentially spaced apart at approximately 90° angles with respect to the axis of the stem and with the intervening stem surfaces being moderately pubescent to glabrous.

C. *Shape.*—Terete.

D. *Size.*—(1) Diameter: Commonly 1.5–5.0 mm. intermediate nodes at maturity. (2) Internode length: Commonly 5–45 mm. between fully developed nodes of mature specimens.

E. *Color.*— (1) General: Commonly uniform epidermal color with occasional variation from one stem to the next. (2) Epidermis: Commonly moderate yellow green (5 GY 6/4) (5 GY 7/4) (5 GY 7/6) (7.5 GY 6/4) and (7.5 GY 7/4).

Leaves:

A. *General.*—Simple, incomplete, petiolate and extipulate. (1) Arrangement: Decussate. (2) Shape: (a) General — generally symmetrical and ovate with occasional elliptical tendencies. (b) Leaf apices — usually obtuse to broadly rounded with occasional acute tendencies. (c) Leaf base — commonly weakly cordate and occasionally showing truncate, oblique and obtuse tendencies. (d) Margins — entire and ciliate with undulate tendencies. (e) Venation — reticulate and pinnate with camptodromous tendencies. (f) Posture — 1. Transverse: Recurved. 2. Longitudinal: Revolute.

B. *Petioles.*—(1) General: Herbaceous. (2) Texture: Three circumferentially spaced apart and longitudinally extending continuous linear rows of hairs that merge at the petiole insertion with the adjacent rows on the stems, there being no row on the adaxial surface. (3) Shape: Elongated and generally obovate to depressed obovate in cross section. (4) Size: (a) Diameter — usually 1–5 mm. intermediate insertion and blades at maturity. (b) Length (insertion to blade base) — usually 3–30 mm. for mature leaves. (5) Color: Commonly moderate yellow green (5 GY 6/4) (5 GY 7/4) (5 GY 7/6) (7.5 GY 6/4) (7.5 GY 7/4).

C. *Leaf blades.*—(1) General: Chartaceous between veins. (2) Texture: Generally glabrous to slightly pubescent with minute hairs and rugose with the left veins protruding at the abaxial leaf surface. (3) Size: (a) Length — usually 30–110 mm. at maturity. (b) Width (maximum) — usually 20–75 mm. at maturity. (4) Color: (a) General — variegated upper epidermis with a basic chlorophyllous field that is normally lighter than the 'Nerve Plant' field coloration but which occasionally shows reversionary tendencies, and with marginally located irregular achlorophyllous blotches and/or flecks, the colors and patterns being somewhat obscured at the abaxial blade side by the translucent and glaucous nature of the lower epidermis. (b) Basic chlorophyllous field — commonly grayish yellow green (5 GY 5/2), moderate yellow green (5 GY 6/4) (5 GY 7/4) (5 GY 5/4) (7.5 GY 5/4), moderate olive green (7/5 GY 4/4) and/or light yellow green (5 GY 8/4) in typical nonreversionary areas. (c) Achlorophyllous blotches and flecks — commonly yellowish white (5 Y 9/1) (5 Y 9/2) (7.5 Y 9/2) (10 Y 9/1); pale yellow (5 Y 9/4) (5 Y 9/2) (7.5 Y 9/2); pale greenish yellow (7.5 Y 9/4) and/or translucent white.

Inflorescences:

A. *Form.*—A terminal spike with structural characteristics normally identifiable with the 'Nerve plant' variety.

B. *Peduncle.*—(1) General: Fleshy. (2) Texture: Wooly. (3) Shape: Terete with slight thinning taper from emergence at stem to bract emergence. (4) Size: (a) Length — generally 35–95 mm. (b) Diameter — usually less than 3 mm. (5) Color: Moderate yellow green (5 GY 7/4) (5 GY 7/6) and/or light yellow green (5 GY 8/4) (5 GY 8/6).

C. *Bracts.*—(1) General: Fleshy and persistent. (2) Shape: Ovate. (3) Size: (a) Length — usually 2–15 mm. at maturity. (b) Maximum width — usually 2–8 mm. at maturity. (4) Color: (a) General — commonly a chlorophyllous center area and achlorophyllous margins, the chlorophyllous area sometimes extending to the margins, and the color being somewhat obscured at the abaxial side by the translucent and glaucous nature of the epidermis. (b) Chlorophyllous area — commonly grayish yellow green (5 GY 6/2) (7.5 GY 6/2) and/or moderate yellow green (5 GY 6/4) (5 GY 5/6) (5 GY 5/4) (7.5 GY 6/4) (7.5 GY 5/6) (7.5 GY 5/4). (c) Achlorophyllous area — commonly yellowish white (5 Y 9/1) (near 5 Y 9/2) (near 7.5 Y 9/2) (near 10 Y 9/1), pale yellow (near 5 Y 9/4) (near 5 Y 9/2) (near 7.5 Y 9/2) and/or pale greenish yellow (7.5 Y 9/4).

D. *Flower.*—(1) General: Small, complete, perfect flowers born in the axils of bracts. (2) Length: Usually 14–24 mm. at maturity. (3) Calyx: (a) General — deeply cut lanceolate sepals. (b) Length — usually 2–6 mm. at maturity. (4) Corolla: (a) General — funnelform like with slender tube and two lipped distally. (b) Length — usually 12–22 mm. at maturity. (c) Color — commonly pale greenish yellow (7.5 Y 9/4) (10 Y 9/4) and/or light yellow green (near 2.5 GY 9/4) in the proximal area and light greenish yellow (7.5 Y 9/8) (7.5 Y 9/6) (near 10 Y 9/6) (near 10 Y 9/8) and/or brilliant greenish yellow (near 7.5 Y 9/8) (near 10 Y 9/8) in distal area. (5) Androecium: (a) General — two epipetalous stamens inserted on midportion of corolla and with pubescent filament and versatile anthers. (b) Filament length — commonly 3–8 mm. at maturity. (6) Gynoecium: (a) General — a filiform style with non-lobed stigma. (b) Length — usually 12–22 mm. at maturity.

The follwing is a general description of a plant of the new variety which was propagated from a stem cutting, the description being taken in the month of November about four months after the cutting was first planted in a nursery at Winter Garden, Fla.

A. *Stems.*—(1) Number of stems developed from initial cutting: 2. (2) Length: 64 mm. and 53 mm. (3) Total number of stem anodes: 5. (4) Diameter: Ranges from 2.5 to 4 mm. (5) Internode length:

Ranges from 11 to 38 mm. (6) Color: Moderate yellow green (5 GY 6/4) (7.5 GY 6/4).

B. *Leaves.*—(1) Number of nonembrionic leaves: 12 excluding leaves on initial cutting. (2) Petioles: (a) Diameter — ranges from 2 to 3 mm. (b) Length — varies from 5 to 18 mm. (c) Color — moderate yellow green (5 GY 6/4) (near 7.5 GY 6/4). (3) Blades: (a) Maximum width — varies from 25 to 67 mm. (b) Maximum length — varies from 49 to 91 mm. (c) Color — 1. Upper epidermis: Moderate yellow grren (7.5 GY 5/4) (5 GY 6/4) and/or grayish yellow green (near 7.5 GY 5/2) (5 GY 5/2) in chlorophyllous areas and yellowish white (5 Y 9/1) (near 10 Y 9/1) in achlorophyllous areas. 2. Lower epidermis: Grayish yellow green (near 7.5 GY 5/2) and/or moderate yellow green (7.5 GY 5/4) (5 GY 6/4) in chlorophyllous areas and yellowish white (5 Y 9/1) (near 10 Y 9/1) in achlorophyllous areas.

The following is a general description of a typical inflorescence which appeared on a plant about six months old from initial propagation.

A. *Peduncle.*—1. Size: (a) Length — 72 mm. (b) Diameter — 2 mm. 2. Color: Moderate yellow green (5 GY 7/4).

B. *Bracts.*—1. Size: (a) Length — varies from 4 to 10 mm. (b) Maximum diameter — varies from 3 to 5 mm. 2. Color: Grayish yellow green (5 GY 6/2) (7.5 GY 6/2) and moderate yellow green (5 GY 6/4) (near 7.5 GY 6/4) in chlorophyllous center area and yellowish white (5 Y 9/1) (near 5 Y 9/2) and pale yellow (near 5 Y 9/2) in achlorophyllous areas.

C. *Flowers.*—1. Number of open flowers: 1. 2. Size: (a) Overall length — 19 mm. (b) Sepal length — 3.5 mm. (c) Corolla length — 15 mm. 3. Corolla color: Pale greenish yellow (10 Y 9/4) in the proximal area and light greenish yellow (7.5 Y 9/6) (7.5 Y 9/8) and brilliant greenish yellow (7.5 Y 9/8) in the distal area.

I claim:

1. The new and distinct variety of the Acanthus family substantially as herein shown and described.

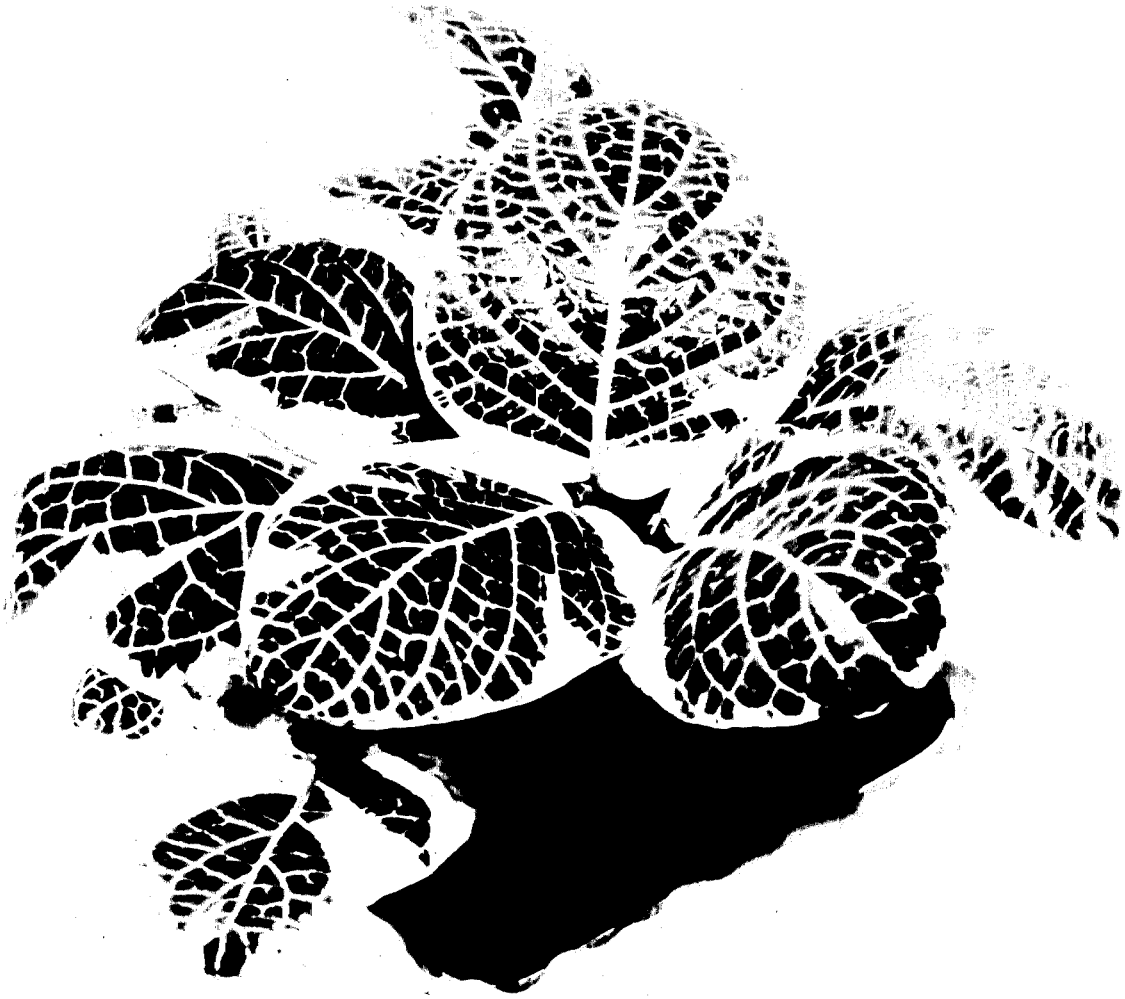

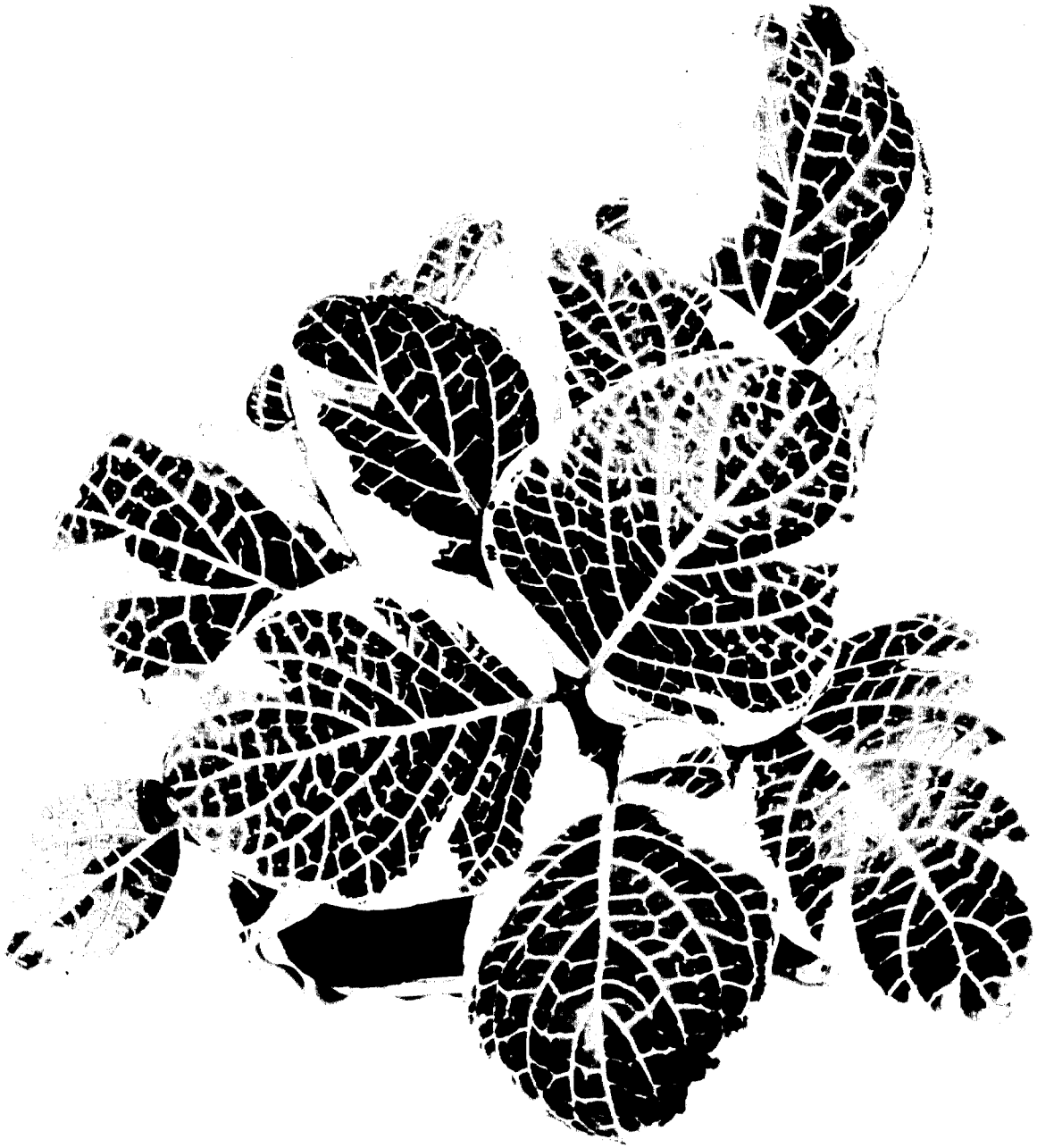

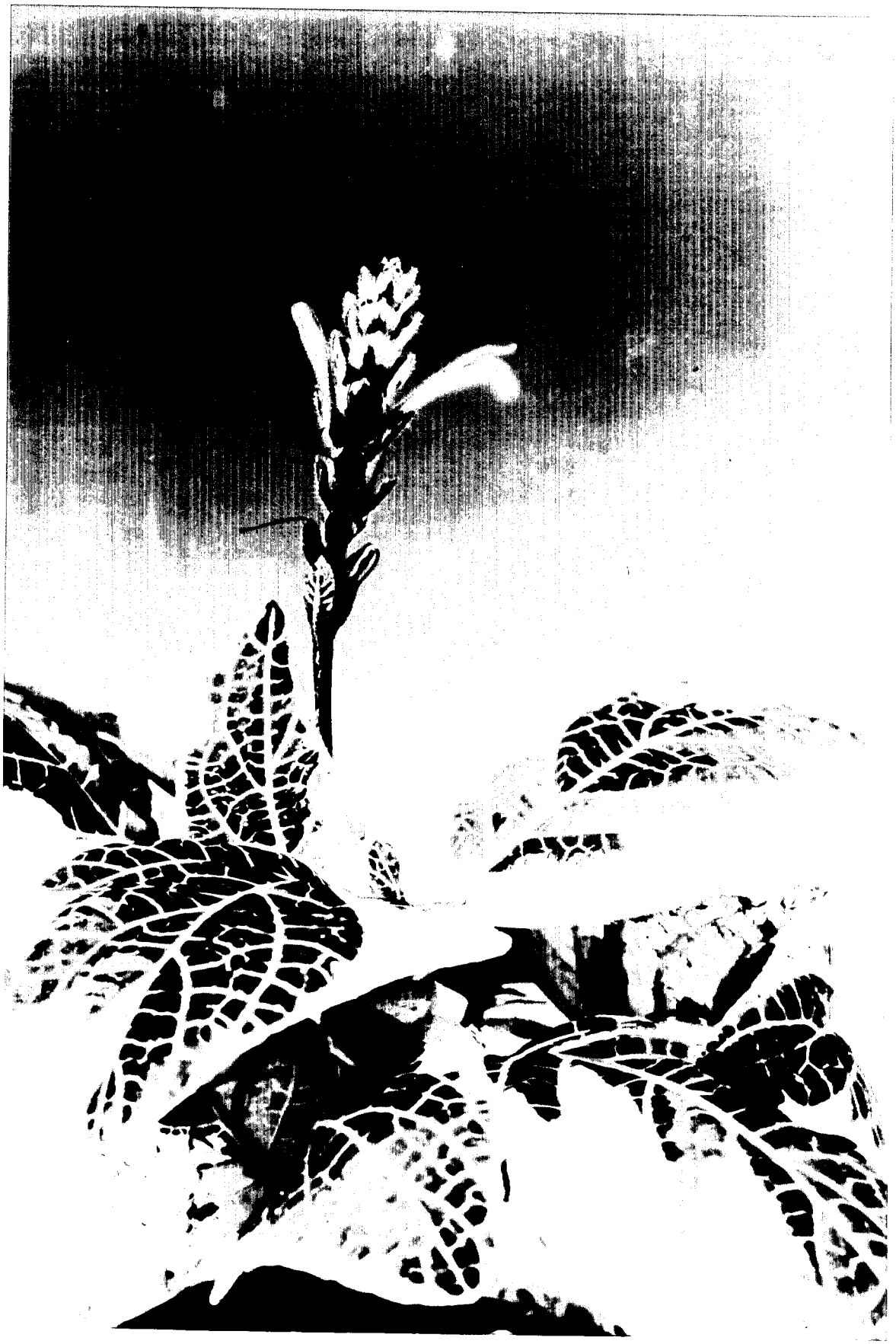

* * * * *